United States Patent [19]

Lohrmann et al.

[11] Patent Number: 5,401,493

[45] Date of Patent: Mar. 28, 1995

[54] PERFLUORO-1H,-1H-NEOPENTYL CONTAINING CONTRAST AGENTS AND METHOD TO USE SAME

[75] Inventors: Rolf Lohrmann, La Jolla; Ashwin Krishnan, San Diego, both of Calif.

[73] Assignee: Molecular Biosystems, Inc., San Diego, Calif.

[21] Appl. No.: 37,279

[22] Filed: Mar. 26, 1993

[51] Int. Cl.$^6$ .................... A61B 5/055; A61K 31/03; C07C 22/00
[52] U.S. Cl. ......................... 424/9; 436/173; 128/653.4; 554/20; 514/533; 514/751; 514/754; 514/832; 570/182
[58] Field of Search ............. 424/9; 436/173; 128/653.4, 654; 554/220; 514/533, 751, 754, 832; 570/182

[56] References Cited

U.S. PATENT DOCUMENTS

| | | | |
|---|---|---|---|
| 4,110,474 | 8/1978 | Lagow et al. | 424/350 |
| 4,187,252 | 2/1980 | Lagow et al. | 260/653 |
| 4,535,184 | 8/1985 | Middleton | 564/102 |
| 4,558,279 | 12/1985 | Ackerman et al. | 324/315 |
| 4,612,185 | 9/1986 | Dean | 424/2 |
| 4,647,447 | 3/1987 | Gries et al. | 424/9 |
| 4,760,173 | 7/1988 | Klaveness | 562/449 |
| 4,775,522 | 10/1988 | Clark, Jr. | 424/9 |
| 4,943,595 | 7/1990 | Sharer et al. | 514/722 |
| 4,957,939 | 9/1990 | Gries et al. | 514/492 |
| 5,116,599 | 5/1992 | Rogers, Jr. et al. | 424/9 |

FOREIGN PATENT DOCUMENTS

PCT/89/06979 8/1989 WIPO.
PCT/90/01792 5/1991 WIPO.

OTHER PUBLICATIONS

Smart et al. J. Am. Chem. Soc. 108:4905–7 (1986).
Dyatkin Russian Chemical Reviews 45(7):607–14 (1976).
Eidelberg et al. Magn. Res. in Medicine 6:344–52 (1988).
James B. Martin, "Preparation of Saturated and Unsaturated Symmetrical Monoglycerides," *The J. of the American Chem. Soc.*, 75:5482 (1953).
Rodgers, et al., *Synthesis of Reporter Groups for Fluorine-19 NMR: A New Class of Imaging and Spectroscopic Compounds*, Abstracts of the Eigth Annual Meeting of the Society of Magnetic Resonance in Medicine (1989) 2:819.
Weichert, et al., *Evaluation of Aryl 3,5-Bistrifluoromethylated Compounds as Potential Fluorine NMR Spectroscopy and Imaging Agents*, Abstracts of the Seventh Annual Meeting of the Society of Magnetic Resonance in Medicine (1988) 1:484.

*Primary Examiner*—Gary E. Hollinden
*Attorney, Agent, or Firm*—Morrison & Foerster

[57] ABSTRACT

Organic compounds for diagnostic imaging which contain at least one aryl group which has been derivatized to contain at least one perfluoro-1H,1H-neopentyl moiety are provided. The perfluoro-1H,1H-neopentyl groups produce a single magnetic resonance to insure a maximum signal to noise ratio. One compound disclosed is 2-O-oleoylglycerol 1,3-bis(7'-{3",5"-di[2''',2'''-di(trifluoromethyl)3''', 3''',3'''-trifluoropropyl]phenyl} heptanoate). In the preferred embodiment, a lipid emulsion is provided as a carrier vehicle to deliver the derivitized analog to a mammalian recipient. Methods to use these compounds in MRI and computerized tomography are provided.

11 Claims, 4 Drawing Sheets

PERFLUORO-1H,-1H-NEOPENTYL CONTAINING CONTRAST AGENTS AND METHOD TO USE SAME

FIELD OF THE INVENTION

This invention relates to organic compounds for diagnostic imaging. In particular, it relates to organic compounds which contain at least one aryl group which has been derivatized to contain at least one perfluoro-1H,1H-neopentyl moiety, and methods for their use. In a specific instance, triglyceride or glycerol phospholipid analogs can be prepared to contain benzyl groups which have been derivatized to contain at least one PFNP moiety. These triglyceride or glycerol phospholipid analogs are useful as hepatic imaging agents.

BACKGROUND OF INVENTION

A number of diagnostic and therapeutic medical procedures require the administration of certain organic compounds as contrast enhancing agents in order to enhance the quality of the procedure. These procedures include: contrast-enhancing agents for Magnetic Resonance Imaging (MRI), Computerized Tomography (CT) and X-ray.

The desire for early detection and treatment of metastatic disease has been the motivation for many recent advances in the fields of radiology and nuclear medicine. In particular, significant advances have been made to improve upon noninvasive techniques for visualizing internal organs using radiography and radioisotope scanning. The use of CT instead of conventional X-ray techniques allows for a more sophisticated visualization of the tissues and organs being studied. In addition, many CT agents have now been developed which provide a further advantage over conventional X-ray radiopaques in that they are more site specific.

Weichert et al. of the University of Michigan have studied the use of halogenated triglyceride compounds as liver and hepatocyte site-specific CT agents. In U.S. Pat. No. 4,873,075, this group at the University of Michigan disclosed polyiodinated triglyceride analogs as radiologic agents. The triglyceride compounds are composed of a triglyceride backbone structure that is 1,3-disubstituted or 1,2,3-trisubstituted with, in some embodiments, a 3-amino-substituted-2,4,6-triiodophenyl aliphatic chain wherein the chain has a structure similar to that of naturally occurring fatty acids.

MRI as opposed to CT has the advantage that it exhibits superior soft tissue differentiation. The two most widespread applications of MRI take advantage of the nuclear magnetic resonance of hydrogen ($^1$H) or fluorine ($^{19}$F). $^{19}$F MRI has the added advantage over $^1$H MRI in that while $^{19}$F has an NMR sensitivity nearly equivalent to that of $^1$H, it demonstrates negligible biological background.

While $^{19}$F MRI provides significant advantages over other imaging techniques, the success of the imaging agents being used depends on such qualities as ease of synthesis, site-specificity, resistance to hydrolysis in-vivo, a sufficient amount of signal and a high signal-to-noise ratio. In some instances, these desired qualities may actually be mutually exclusive. For example, the signal of a $^{19}$F MRI contrast agent can be increased by adding additional fluorines. However, depending on where the fluorine substituents are attached to the imaging agents being used, the fluorine containing molecules may exhibit different spectral resonance lines. This results in insufficient intensity of the signal of interest relative to noise which leads to a low signal-to-noise (S/N) ratio or band broadening and blurred images due to multiple resonances. As a result, high doses of the imaging agent or long imaging times are required.

The use of 3,5-bis(trifluoromethyl)aryl compounds, such as 1,3-bis[3',5'-di(trifluoromethyl)phenylacetyl] 2-oleoyl glycerol, for site-specific delivery of fluorine MRI agents has been disclosed by Weichert et al. (Abstracts of the Seventh Annual Meeting of the Society of Magnetic Resonance in Medicine (1988) 1; 484). This compound has the advantage that it exhibits only a single resonance frequency. However, it suffers from the problem of having only a limited number of fluorine equivalents per molecule.

The problem of insufficiency of signal was addressed by Rogers et al. with the development of perfluoro-tert-butyl (PFTB) reporter groups with each having 9 magnetically equivalent $^{19}$F nuclei. It was recognized that these compounds provide a mono-resonant fluorine reporter group making these types of compounds practical for MRI measurements. Rogers et al., *Synthesis of Reporter Groups for Fluorine*-19 *NMR; a New Class of Imaging and Spectroscopic Compounds*, Abstracts of the Eighth Annual Meeting of the Society of Magnetic Resonance in Medicine (1989) 2, 819; U.S. Pat. No. 5,116,599. However, known methods of introducing PFTB reporter groups are complicated and often involve steps that would destroy the biological activity or geometry of host compounds and thus interfere with their ability to efficiently target specific organs or tissues.

Therefore, there exists a need to provide for a class of $^{19}$F-MRI imaging agents which can overcome the aforementioned disadvantages.

SUMMARY OF THE INVENTION

The present invention provides for PFNP containing contrast agents. These contrast agents include pharmacological and biological compounds rendered active as magnetic resonance imaging agents by being modified to include a phenyl group to which at least one PFNP moiety has been attached. The PFNP groups produce a single magnetic resonance to insure a maximum signal to noise ratio. This reduces the concentration of the agent required for adequate augmentation of the $^{19}$F magnetic resonance signal.

More specifically, the present invention provides a derivatized triglyceride or glycerol phospholipid analog wherein the analog contains at least one PFNP moiety. Glycerol phospholipids are contemplated because of their anticipated low toxicity and desirable amphipathic character.

More specifically, the present invention provides a derivatized triglyceride or glycerol phospholipid analog wherein the analog contains at least one [2,2-di(trifluoromethyl)3,3,3,-trifluoropropyl] moiety. This moiety, which can also be referred to as a perfluoro-1H,1H-neopentyl moiety will hereinafter be referred to as "PFNP".

The novel compounds of the present invention may have the general formula:

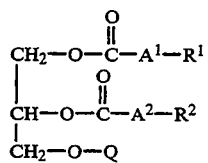

wherein Q is

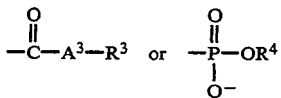

and A¹, A² and A³ are each selected from the group consisting of:

saturated and unsaturated aliphatic hydrocarbon chains;

amine substituted saturated and unsaturated aliphatic hydrocarbon chains; and amide substituted saturated and unsaturated aliphatic hydrocarbon chains;

wherein R¹, R² and R³ are each selected from the group consisting of: $CH_3$; $NH_2$; $CONH_2$; OH; and

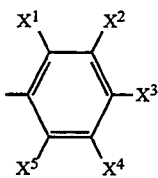

wherein R4, if present, is selected from the group consisting of:

Hydrogen;
Choline;
Ethanolamine;
Serine;
Glycerol;
or myo-Inositol wherein x¹, x², x³, x⁴ and x⁵ are each selected from the group consisting of:

Hydrogen;
Iodine;
$NH_2$;
$CH_3$;
$(CH_2)_nCH_3$;
$(CH_2)_nZ$;
$CH[(CH_2)_nZ]_2$;
and $C[(CH_2)_nZ]_3$;

wherein n=1 to 3 and wherein Z=C(CF₃)₃; with the proviso that at least one of x¹ to x⁵ is selected from the group consisting of:

$(CH_2)_nZ$;
$CH[(CH_2)_nZ]_2$;
and $C[(CH_2)_nZ]_3$.

In another embodiment the novel compounds of the present invention have the general formula:

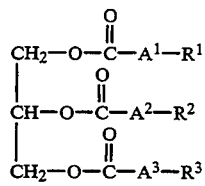

wherein A¹, A² and A³ are each selected from the group consisting of:

saturated and unsaturated aliphatic hydrocarbon chains;

amine substituted saturated and unsaturated aliphatic hydrocarbon chains; and amide substituted saturated and unsaturated aliphatic hydrocarbon chains;

wherein R¹, R², and R³ are each selected from the group consisting of: $CH_3$; $NH_2$; $CONH_2$; OH; and

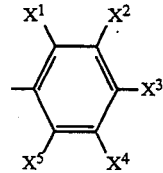

wherein x¹, x², x³, x⁴ and x⁵ are each selected from the group consisting of:

Hydrogen;
Iodine;
$NH_2$;
$CH_3$;
$(CH_2)_nCH_3$;
$(CH_2)_nZ$;
$CH[(CH_2)_nZ]_2$;
and $C[(CH_2)_nZ]_3$;

wherein n=1 to 3 and wherein Z=C(CF₃)₃ with the proviso that at least one of x¹ to X⁵ is selected from the group consisting of:

$(CH_2)_nZ$;
$CH[(CH_2)_nZ]_2$;
and $C[(CH_2)_nZ]_3$.

The novel compounds of the present invention can be more specifically triglyceride analogs having the basic formula:

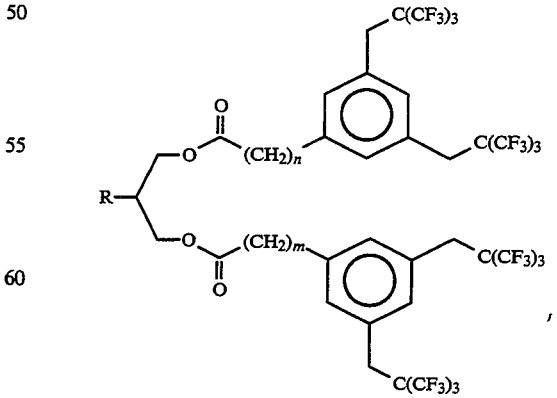

Wherein R is a fatty acyl group with 3-20 carbon atoms, n is 0-18 and m is 0-18. Preferably, n and m are 6. The fatty acid can include saturated or unsaturated aliphatic hydrocarbons of either an even or odd number. Preferably, the triglyceride analog has a low melting point fatty acid such as oleic acid in the 2 position.

In a specific embodiment the PFNP derivatized triglyceride analog is 2-O-oleoylglycerol 1,3-bis(7'-{3'',5''-di[PFNP]phenyl}heptanoate). Preferably, the triglyceride analog is delivered to the patient parenterally as an emulsion. As such, long chain fatty acid compounds (i.e., A having a carbon-skeleton of 8-20 carbons in length) are preferred in that these types of compounds are easier to emulsify.

The analogs of the present invention are useful as MRI agents. Also, if iodine is added to the aryl ring, the compound can be used both as an MRI and CT agent at the same time. As contrast agents, the analogs are liver specific and hepatocyte selective. As radiopaque agents, the analogs find particular applicability as a contrast agent for computerized tomography.

Additionally, this invention provides for bifunctional aryl containing contrast agents derivitized with at least one PFNP moiety and a chelating ligand for a paramagnetic metal. These agents would then be useful for both $^{19}F$ MRI and $^{1}H$ MRI.

The $^{19}F$ NMR spectra of the compounds were carried out with a Varian, GEMINI-200 MHz NMR instrument model number 958562-14. The spectra were taken in deutero chloroform containing 0.3% freon as internal reference. The chemical shifts of the observed peak were determined with reference to freon. The use of a standard sign convention of (+) signals downfield from (left of freon) and (−) upfield from (right of Freon) was adopted. Vast majority of organic fluorine compounds have signals which are negative. The +50 to −250 ppm range covers most compounds. The triglyceride example shown exhibited one single peak for all the 36 fluorines at −65.16 ppm from freon.

Figure 4:
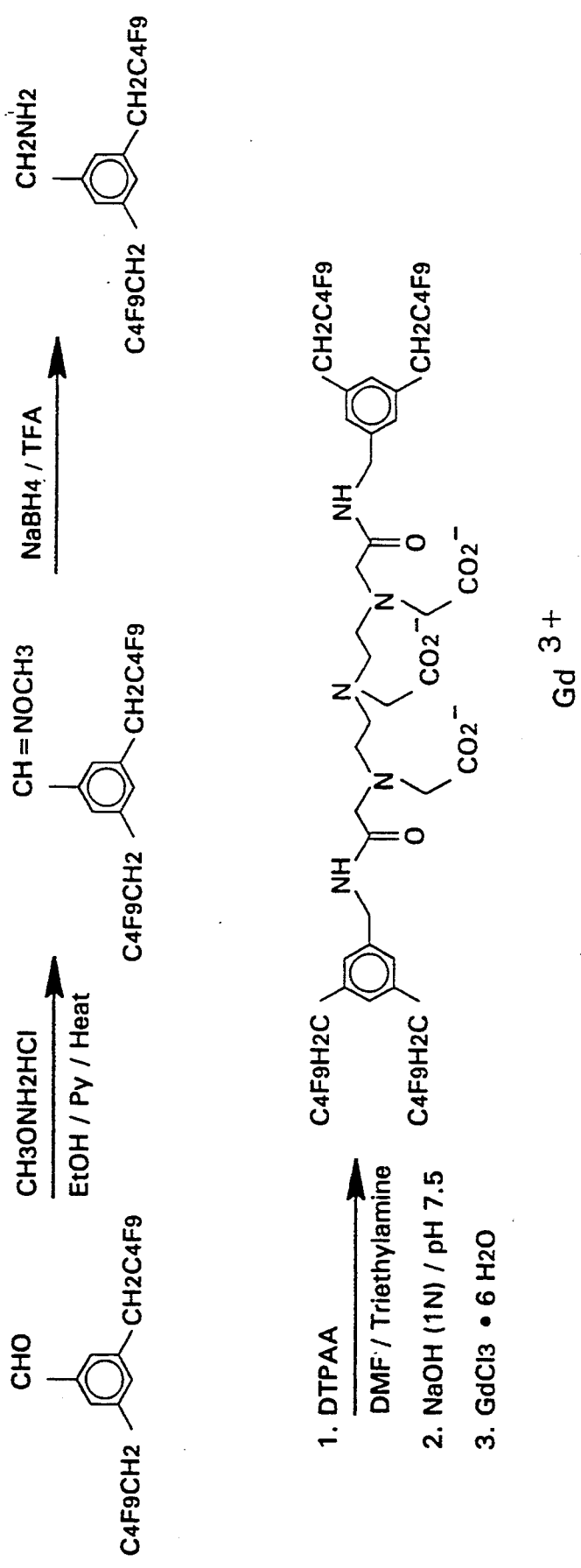

FIG. 4 shows synthesis route to make a gadolinium chelate.

DETAILED DESCRIPTION OF THE INVENTION

This invention is based on the discovery that a large number of magnetically equivalent fluorines can be added to biological or pharmaceutical compounds to render these compounds active as nuclear magnetic resonance spectroscopy or magnetic resonance imaging agents by being modified to include aryl groups to which at least one PFNP group has been attached. When the PFNP group is the only source of fluorine, it provides for a source of nine magnetically equivalent fluorine nuclei and produces a single magnetic resonance with a maximum signal to noise ratio. This in turn reduces the concentration of the agent required for adequate detection, reduces imaging time, and permits the use of lower field strength MR imaging systems.

The PFNP phenyl group may be added to a variety of biological or pharmaceutical compounds. The biological or pharmaceutical compounds contemplated by the present invention include amino acids, amino acid analogs, polypeptides, proteins, lipoproteins, fatty acids, triglycerides, glycerol phospholipids, steroids dendrimers or polysaccharides.

Additionally, multi-functional contrast agents providing for MRI (both $^{19}F$ and $^{1}H$) and computerized tomography are contemplated. For example, the biological or pharmaceutical compounds can be iodinated, or the phenyl groups attached thereto can be iodinated. The aryl groups to which at least one PFNP moiety has been added can be incorporated into a chelating ligand such as diethylenetriamine pentaacetic acid. See Greis U.S. Pat. No. 4,647,447, Klaveness WO 89/06979; Cockbain WO 91/05762. This chelating ligand can be used to chelate gadolinium and would be useful for enhancing NMR images. See Greis U.S. Pat. No. 4,957,939. Additionally, dendrimers such as STARBURST (Dow Chemical Co.) polymers can be used to hold multiple chelating ligands incorporating perfluoro-1H1H-neopentyl aryl substituents. See Tomalia U.S. Ser. No. 897,455 (hereby incorporated by reference).

The electronic and steric features of an aromatic system allows easy multiple substitutions. In addition, it permits the introduction of iodines in the presence of PFNP moieties. This enables the synthesis of multifunctional imaging agents, for example for MRI and CT. Adding a PFNP moiety to an aryl group, as opposed to a multiply fluorine-substituted alkyl compound, allows one to take advantage of the electronic and stearic features of aromatic rings. These advantages include the ability to add multiple perfluoro-1H,1H-neopentyl groups per aromatic ring, the ability to create multifunctional imaging agents by also adding iodine to the phenyl group rendering the agent active as both an MRI and CT agent, and the ability to take advantage of the inherent hydrophobicity of the aryl group.

In particular, the method of synthesizing contrast agents which contain a phenyl group having at least one perfluoro-1H,1H-neopentyl moiety has advantages over the method of synthesizing fluorinated contrast agents using aliphatic halides. The benzyl halides used in synthesizing the contrast agents of the present invention react faster with carbanion intermediates such as $C_4F_9-Cs^+$ and exhibit substantially better yields than aliphatic halides. Additionally, unreacted benzyl halides are more easily removed from the reaction mixture. Also, benzyl halides are readily available, being prepared by using any suitable means of halogenating benzyl-containing compounds, and can be multiply substituted with a variety of functionalities. In particular, the benzyl moiety allows for the addition of multiple perfluoro-1H,1H-neopentyl moieties as well as iodine.

It should be recognized that a suitable carrier is needed if the biological or pharmaceutical compound is not soluble in water. The soluble carriers include lipid emulsions, liposomes, microparticles or microspheres. If the biological or pharmaceutical compound is water soluble a carrier is not required.

In a preferred embodiment of the invention, which will be discussed in greater detail below, the lipophilic nature of the triglyceride analog, in particular 2-O-oleoylglycerol 1,3-bis(7'-{3'',5''-di[PFNP]phenyl}heptanoate) (FIGS. 1,9), enables these analogs to be incorporated into a suitable carrier such as a fat emulsion which upon administration to a patient is rapidly sequestered by the hepatocytes in the liver.

The above discussed triglyceride analogs may be administered to mammalian subjects as radiologic agents by a known manner, such as by intraveneous injection. For hepatic imaging, intravenous administration is the preferred route. A transport agent, however, is required for these analogs, such as a lipid emulsion. See U.S. Pat. No. 4,873,075 (hereby incorporated by reference) for a description of emulsions that would be suitable as carriers for the presently disclosed triglyceride analogs.

The following section discloses the synthesis process that provides the following advantages. The intervening methyl group between the fluorine moiety and the aryl compound facilitates coupling of multiple polyfluorinated groups. In the preferred embodiment shown in FIG. 1, 36 magnetically equivalent fluorines are held on an aryl-containing triglyceride analog.

EXAMPLE 1

Synthesis of 2-O-oleoylglycerol 1,3-bis(7'-{3'', 5''-di[PFNP]phenyl}heptanoate)

Melting points are uncorrected. Nuclear magnetic resonance spectra were obtained using a 200 MHz instrument tuned for determination of proton ($^1$H) or fluorine ($^{19}$F) resonances.

1-Bromo-3,5-bis(bromomethyl)benzene (FIG. 1, 1) was prepared by adding bromine (65.2 g, 0.408 mol) dropwise to a solution of 1-bromo-3,5-dimethylbenzene (38.11 g, 0.206 mol) in carbon tetrachloride (350 ml), which was irradiated with a 300 watt General Electric Tungsten lamp. Under these conditions bromine uptake was fast as indicated by the disappearance of the red color. Hydrogen bromide gas evolved and was scrubbed into 10% sodium hydroxide solution. The bromine was completely added in 75 minutes. Irradiation and stirring was continued at ambient temperature for two more hours. The mixture was then diluted with water (100 ml). The carbon tetrachloride layer was separated and washed with water (300 ml). The organic layer was dried (anhydrous sodium sulfate). After filtration, volatile solvents were removed under vacuum. 1-Bromo-3,5-bis(bromomethyl)benzene crystallized on trituration of the residual oil with hexane (150 ml); 27.6 g (0.08 mol, 39% of theoretical) of product was obtained. The melting point of the composition was 90°–93° C.

The $^1$H NMR spectrum in CDCl$_3$ showed the following resonances relative to TMS: 7.48 (s, 1H, aromatic), 7.35 (s, 2H, aromatic), and 4.42 (s, 4H, CH$_2$) ppm.

Next, 1-bromo-3,5-bis[PFNP]benzene (FIG. 1, 2) was prepared. In a flask equipped with a gas inlet, mechanical stirrer and a dry ice condenser was placed a suspension of dry cesium fluoride (31.0 g, 0.20 mol) in monoglyme (200 ml). Perfluoroisobutylene gas (40.0 g, 0.20 mol) was bubbled in. The gas reacted rapidly with cesium fluoride and a yellow solution resulted. The mixture was stirred for one hour, and then a solution of 1-bromo-3,5-bis(bromomethyl)benzene (FIG. 1, 1) (30.0 g, 0.087 mol) in monoglyme (50 ml) was added dropwise. The resulting reaction was slightly exothermic and caused cesium bromide to precipitate from solution. The mixture was stirred overnight and the precipitated salt was removed by filtration. The filtrate was concentrated under vacuum, and the residue was taken up in dichloromethane (120 ml). The organic layer was washed with water (50 ml) and then was dried (anhydrous sodium sulfate). After filtration, the solvent was removed under vacuum. The residue was crystallized from a mixture of hexane and ether (10:90, v/v) to provide 1-bromo-3,5-bis[PFNP]benzene as colorless crystals (45.84 g 0.073 mol, 85%, m.p. 120°–121° C).

Its $^1$H NMR spectrum in CDCl$_3$ solution showed the following resonances relative to TMS: 7.44 (s, 2H, aromatic), 7.20 (s, 1H, aromatic), and 3.37 (s, 4H, CH$_2$) ppm. Its $^{19}$F NMR spectrum in CDCl$_3$ showed a single resonance at −65.58 (s, 18 F) ppm relative to Freon.

Figure 1:
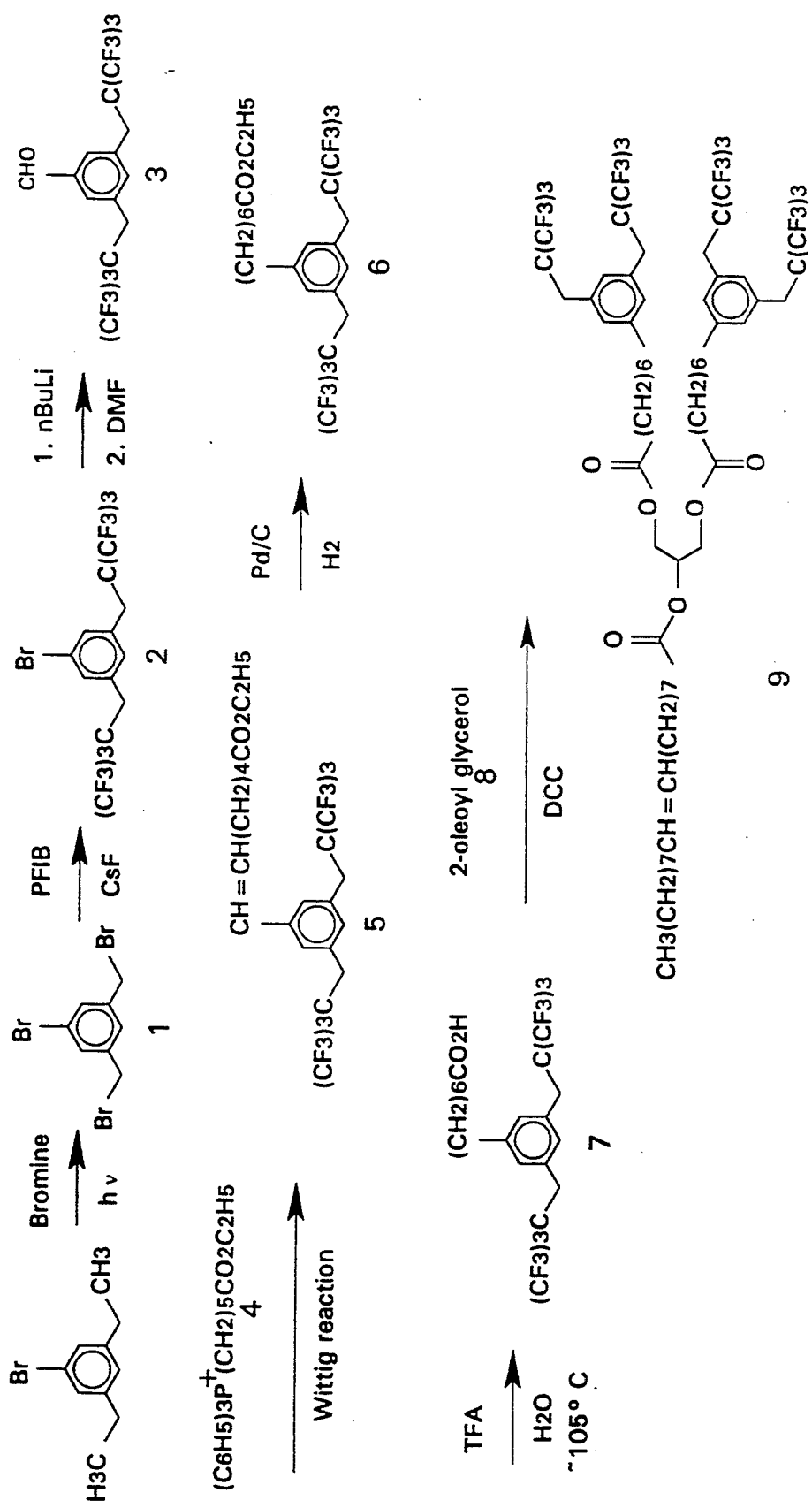
FIG. 1 shows the synthesis scheme for 2-O-oleoylglycerol 1,3-bis(7'-{3'',5''-di[PFNP]phenyl}heptanoate).

1-Formyl-3,5-bis(PFNP)benzene (FIG. 1, 3) was prepared in a dry flask under argon atmosphere. A solution of 1-bromo-3,5-bis(PFNP)benzene (FIG. 1, 2) (24.3 g, 0.039 mol) in diethyl ether (300 ml) was cooled to −60° C. in a dry ice/acetone bath, and 2.5N n-butyl lithium in hexane (18 ml, 0.045 mol) was added dropwise with stirring. After the addition was completed, the mixture was gradually warmed to 0° C. and then cooled again to −50° C. Dimethylformamide (60 ml) was added dropwise. The resulting reaction was slightly exothermic. The mixture was warmed to room temperature and allowed to stand overnight. After the addition of water (30 ml), organic solvents were removed under vacuum. The residue, which contained small amounts of dimethylformamide, was mixed with water, and the mixture was extracted with dichloromethane (200 ml). The dichloromethane extract was dried (anhydrous sodium sulfate). After filtration, the dichloromethane extracts were allowed to stand and gradually deposited crystalline material which was isolated by filtration. The filtrand was identified as 1-formyl-3,5-bis(PFNP)benzene (FIG. 1, 3). Additional compound was obtained on concentration of the filtrate to give a total of 17.8 g of material (0.023 mol, 77% of theoretical). The melting point of the composition was 128°–130° C. The purified composition was found to be homogeneous on TLC (silica gel, Rf=0.45 after elution with dichloromethane/hexane, 4:6, v/v).

By elemental analysis the compound contained (calculated for C$_{17}$H$_8$F$_{18}$O) C, 36.03 (35.78); H, 1.35 (1.40); F, 59.69 (60.0). The $^1$H NMR spectrum of its CDCl$_3$ solution showed the following resonances relative to TMS: 9.98 (s, 1H, CHO), 7.78 (s, 2H, aromatic), 7.51 (s, 1H, aromatic), and 3.47 (s, 4H, CH$_2$) ppm. Its $^{19}$F NMR spectrum in the same solvent showed a single resonance at −65.57 (s, 18F) ppm relative to Freon.

In the next step 7-[3',5'-bis(PFNP)phenyl]hept-6-enoic acid ethyl ester (FIG. 1, 5) was prepared. Using a dry flask and an argon atmosphere, 1.5N lithium diethylamide (LDA) in tetrahydrofuran (19 ml, 0.029 mol) was added dropwise to a stirred solution of 5-(ethoxycarbonyl)pentyltriphenylphosphonium bromide (FIG. 1, 4) (11.4 g, 0.027 mol) in dimethylformamide (35 ml) that had been cooled to −60° C. The reaction mixture turned yellow during the addition of LDA solution. After complete addition, the mixture was warmed to −5° C. and then again cooled to −50° C. A solution of 1-formyl-3,5-bis(PFNP)benzene (15.07 g, 0.025 mol) in warm dimethylformamide (100 ml) was added dropwise with stirring at a rate that kept the reaction temperature below −40° C. The resulting mixture was allowed to warm to room temperature and was stirred overnight, during which time the solution became clear. Dimethylformamide was then removed under reduced pressure. The residue was diluted with water (100 ml) and extracted with dichloromethane (225 ml). The dichloromethane extract was dried (anhydrous sodium sulfate), filtered and concentrated under reduced pressure. The residual, yellow, viscous material was a mixture by thin layer chromatographic (TLC) analysis (silica gel, hexane/dichloromethane, 1:1, v/v). The desired product, 7-[3',5'-bis(PFNP)phenyl]hept-6-enoic acid ethyl ester, was separated from the mixture by column chromatography on silica gel. Elution with a mixture of hexane/dichloromethane (1:1, v/v) initially furnished some starting materials, followed by the pure product, which was isolated as a viscous oil (6.12 g, 0.0087 mol, 34% of theoretical). The oil, 7-[3',5'-bis(PFNP)phenyl]hept-6-enoic acid ethyl ester, was homogeneous by TLC (silica gel, Rf=0.6 following elution with dichloromethane/hexane, 4:6, v/v).

The $^1$H NMR spectrum of its CDCl$_3$ solution showed the following resonances: 7.23 (s, 2H, aromatic), 7.11 (s, 1H, aromatic), 6.38 (d, 1H, =C$\underline{H}$), 5.70 (m, 1H, C$\underline{H}$), 4.14 (q, 2H, OC$\underline{H}_2$), 3.41 (s, 4H, C$\underline{H}_2$), 2.28 (m, H, C$\underline{H}_2$), 1.58 (m, 4H, C$\underline{H}_2$), and 1.27 (t, 3H, C$\underline{H}_3$) ppm.

The above compound was converted to 7-[3',5'-bis(PFNP)phenyl]heptanoic acid ethyl ester (FIG. 1, 6). 7-[3',5'-bis(PFNP)phenyl]hept-6-enoic acid ethyl ester (FIG. 1, 5) (5.98 g, 0.009 mol) was dissolved in ethanol (125 ml), palladium on charcoal (10%, 0.21 g) was added, and the suspension was hydrogenated at 50 psi until hydrogen uptake ceased. The catalyst was removed by filtration, and the ethanol was evaporated to provide crude 7-[3',5'-bis(PFNP)phenyl]heptanoic acid ethyl ester (FIG. 1, 6) as an oil (5.91 g, 0.0085 mol, 99% of theoretical). The product was homogeneous by TLC (Rf=0.6, silica gel eluted with hexane/dichloromethane, 3:1, v/v).

By elemental analysis the compound contained (calculated for C$_{17}$H$_8$F$_{18}$O) C, 36.03 (35.78); H, 1.35 (1.40); F, 59.69 (60.0). The $^1$H NMR spectrum of its CDCl$_3$ solution showed the following resonances relative to TMS: 7.23 (s, 1H, aromatic), 7.11 (s, 1H, aromatic), 4.12 (q, 2H, OC$\underline{H}_2$), 3.34 (s, 4H, C$\underline{H}_2$), 2.54 (t, 2H, C$\underline{H}_2$), 2.25 (t, 2H, C$\underline{H}_2$), 1.55 (m, 4H, C$\underline{H}_2$), 1.27 (m, 4H, C$\underline{H}_2$), and 1.22 (t, 3$\underline{H}$, C$\underline{H}_3$) ppm. The $^{19}$F NMR spectrum of its CDCl$_3$ solution consisted of a single resonance at −65.51 (s, 18F) ppm relative to Freon.

Next, 7-[3',5'-bis(PFNP)phenyl]heptanoic acid (FIG. 1, 7) was made by dissolving 7-[3',5'-bis(PFNP)phenyl]heptanoic acid ethyl ester (FIG. 1, 6) in trifluoroacetic acid (TFA) solution (50 ml TFA and 5 ml water) and heating under reflux at 105° C. bath temperature for twenty hours. The mixture was cooled, and most of the trifluoroacetic acid was removed under reduced pressure. The residue was diluted with water (50 ml) and then titrated with 10% sodium hydroxide solution to pH 2.3. The aqueous solution was extracted in dichloromethane (200 ml), and the organic extract was washed with water (25 ml). Then the extract was dried (anhydrous sodium sulfate), filtered and concentrated under vacuum to furnish pure 7-[3',5'-bis(PFNP)phenyl]heptanoic acid (FIG. 1, 7) as an oil (5.22 g, 0.0078 mol, 92% of theoretical).

The $^1$H NMR spectrum of its CDCl$_3$ solution showed the following resonances relative to TMS: 7.26 (s, H, aromatic), 7.05 (s, 2H, aromatic), 3.37 (s, 4H, C$\underline{H}_2$), 2.58 (t, 2H, C$\underline{H}_2$), 2.34 (t, 2H, C$\underline{H}_2$), 1.58 (m, 4H, C$\underline{H}_2$), and 1.34 (m, 4H, C$\underline{H}_2$) ppm; the COOH proton was observed as a very broad resonance. The $^{19}$F NMR spectrum consisted of a single resonance at −65.54 (s, 18F) relative to Freon.

2-Oleoyl glycerol was prepared by treatment of 1,3-benzylideneglycerol with oleoyl chloride in the presence of an equivalent quantity of pyridine in chloroform solution. The crude product is treated with boric acid in triethyl borate and heated at 100° C. The solvent was removed after 30 minutes and the residue extracted in diethyl ether. Removal of ether furnished the crude oleoyl glycerol which was purified by crystallization from cold petroleum ether kept below −15° C. The compound which was an oil at room temperature, was sufficiently pure to use without further purification. The 1,3-benzylidenglycerol was prepared by refluxing a solution of glycerol, benzaldehyde and p-toluenesulfonic acid (catalyst), in toluene. Concentration of toluene and cooling furnished the benzylideneglycerol as colourless crystals, additional material was obtained from the filtrates on standing, to furnish excellent yields of the product. Martin, *The J. of the American Chem. Soc.*, 75:5482 (1953).

In the final step of the synthesis 1,3-bis{7-[3',5'-di(PFNP)phenyl]heptanoyl} 2-oleoyl glycerol ester (FIG. 1, 9) was prepared by dissolving 2-oleoyl glycerol (1.40 g, 0.004 mol) and 7-[3',5'-bis(PFNP)phenyl]heptanoic acid (FIG. 1, 7) (5.1 g, 0.0076 mol) in dichloromethane (25 ml) in a dry flask under an argon atmosphere and then adding a solution of dicyclohexylcarbodiimide (91.7 g, 0.008 mol) in dichloromethane (25 ml) with stirring. The mixture was initially cooled to 10° C. and then slowly warmed to room temperature. A small amount of dimethylaminopyridine (0.04 g, 0.0003 mol) was added when a solid began to precipitate. The reaction mixture was stirred overnight, and the precipitated dicyclohexylurea was removed by filtration. The filtrate was concentrated under vacuum, and the residue was chromatographed on silica gel. Elution with hexane/dichoromethane (1:1, v/v) furnished initially some impurities followed by 1,3-bis{7'-[3'',5''-di(PFNP)-phenyl]heptanoyl} 2-oleoyl glycerol ester (FIG. 1, 9). The glyceryl ester was eluted completely with dichloromethane and was obtained as a colorless viscous oil (6.17 g, 0.0037 mol, 95% of theoretical). The ester was homogeneous by TLC (silica gel, R$_f$=0.6 after elution with dichloromethane/hexane, 3:7, v/v).

By elemental analysis the ester contained (calculated for C$_{67}$H$_{76}$O$_6$F$_{36}$): C, 48.42% (48.43%); H, 4.56% (4.57%); F, 40.56% (41.20%). Its $^1$H NMR spectrum (CDCL$_3$ solution) consisted of the following resonances relative to TMS: 7.22 (s, 1H, aromatic), 7.03 (s, 2H, aromatic), 5.31 (m, 3H, C$\underline{H}$), 4.06–4.03 (m, 4H, OC$\underline{H}_2$), 3.34 (s, 8H, C$\underline{H}_2$), 2.54 (t, 6H, C$\underline{H}_2$), 2.27 (t, 6H, C$\underline{H}_2$), 1.98 (m, 4H, C$\underline{H}_2$), 1.47–1.55 (m, 14H, C$\underline{H}_2$), 1.24–1.26 (m, 28H, C$\underline{H}_2$), 0.85 (t, 3H, C$\underline{H}_3$) ppm. Its $^{19}$F NMR spectrum in the same solvent consisted of a single resonance at −65.16 (s, 36F) ppm relative to Freon. Additionally, mass spectral analysis of the final product showed the following: M+ =1660, and major peaks at m/e 1379 (M=−281), 991, 653, 569, and 555 (base peak).

In Vivo Imaging 2-oleoyl glycerol -1,3-bis-(7'{3'',5''-di[PFNP]-phenyl)heptanoate) was prepared as described and emulsified in an oil-in-water emulsion containing a cholesterol:phosphatidyl choline ratio of 0.4 and a final volume of 10% (See also U.S. Pat. No. 4,873,075). An imaging dose of this emulsion was then injected intravenously into a rat.

Figure 2A:
FIG. 2A shows photographs of $-^{1}H$ MRI images for the tests discussed in Example 1.
Figure 2B:
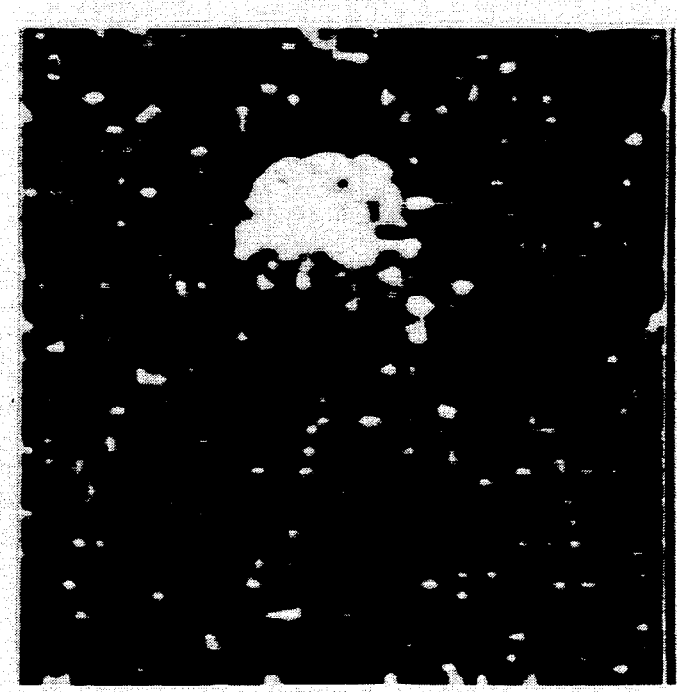
FIG. 2B shows photographs of $-^{19}F$ MRI images for the tests discussed in Example 1.
Figure 3:
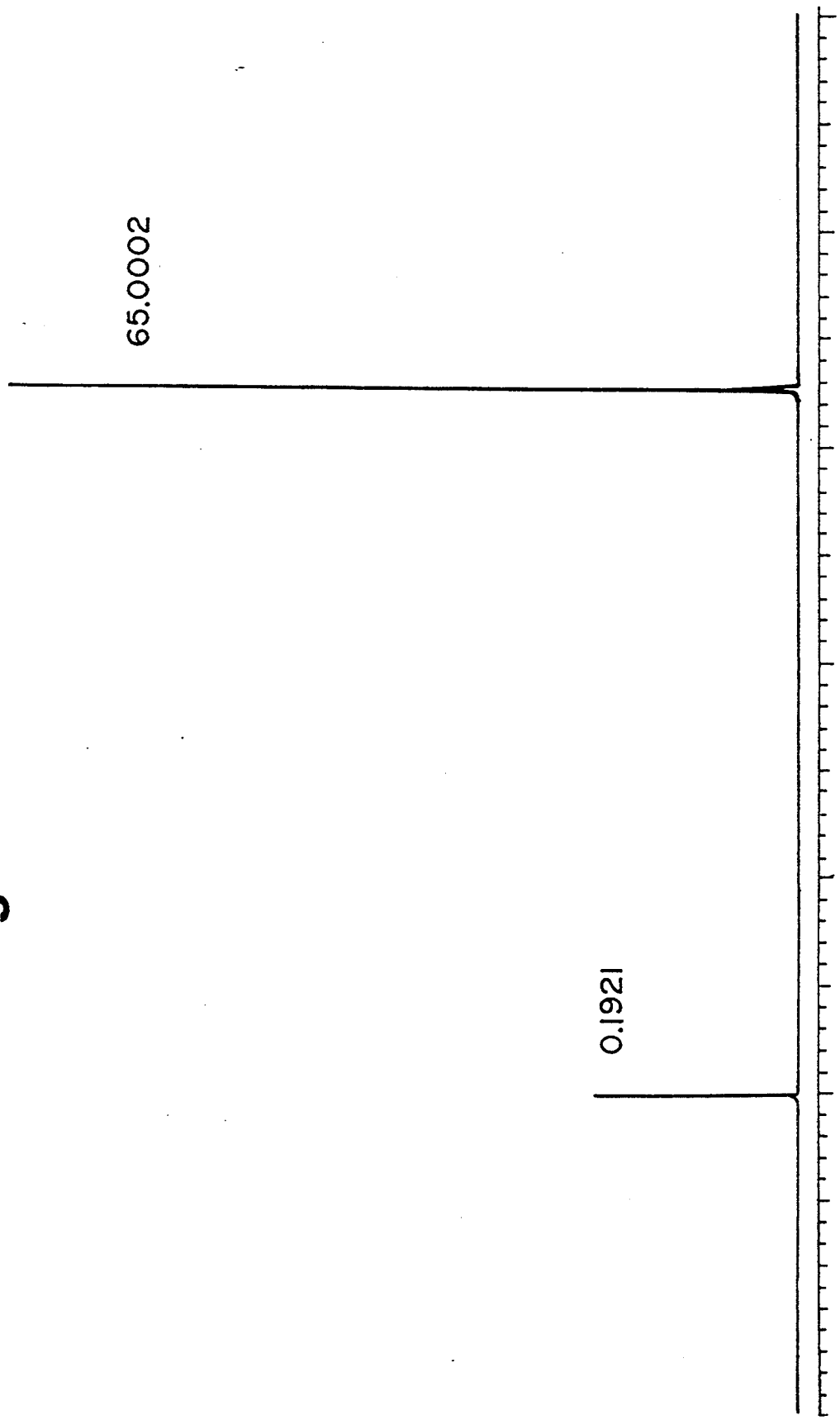
FIG. 3 shows the $^{19}F$ spectra of 2-O-oleoylglycerol 1,3-bis(7'-{3'',5''-di[PFNP]phenyl}heptanoate).

Proton ($^1$H) and Fluorine ($^{19}$F) MRI studies were performed at 4.7 tesla using a purpose-built radio-frequency (RF) coil. See FIG. 2A and 2B respectively. The RF coil allows for "whole-body" imaging of rats and is tuneable to both protons and fluorine resonance frequencies so that the subject need not be moved during the MRI study. The proton MRI utilized the following parameters: Repetition time (TR)=1 second, echo time (TE)=18 milliseconds, image data matrix=128×128, number of excitations (NEX)=2, field of view (FOV)=128 nm, and slice thickness=2.5 or 5.0 mm. The fluorine MRI utilized the following parameters: TR=1 second, TE=18 milliseconds, image data matrix =64×64, NEX=32, FOV=128 nm, and slice thickness was not selected.

Proton and fluorine MRI were done before and after administration of the contrast agent emulsion. Proton MRI was used to provide anatomic markers for assessment of the fluorine images. When evaluating the proton MRI imaging results, the pre- and post-contrast images did not change in qualitative appearance. In the fluorine MRI study, there was no detectable signal in the pre-contrast agent images. Forty five minutes after injection of the contrast agent emulsion, a discernable fluorine MR image of the liver and upper intestinal lumen (indicative of biliary excretion) was typically seen. The signal-to-noise ratio for these images for the parameters noted above was generally 2 to 3. See FIG. 2.

EXAMPLE 2

Triglyceride containing both perfluoro-1H,1H-neopentyl phenyl groups and iodine containing aromatic rings can be prepared. In a typical example, glycerol 2-{7'(3",5"-bis [PFNP]phenyl) heptanoyl}-1,3 bis-(7'{3'-amino-2',4',6'-triiodophenyl}heptanoate) can be obtained by acylation of glycerol with 7-(3',5'-bis[PFNP]phenyl) heptanoic acid in the 2 position, followed by 1,3 acylation with two equivalents of the 7-[3'-amino-2',4',6'-triiodo phenyl} heptanoic acid in an inert solvent in the presence of a base such as 4-N,N-dimethylamino pyridine and dicylohexyl carbodiimide at room temperature as previously described.

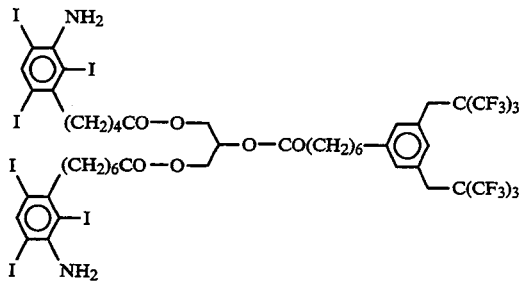

EXAMPLE 3

The PFNP groups can be incorporated in the synthesis of a polypeptide or protein molecules to afford compounds as potential MRI agents. In a typical example, the 4-bromo benzylbromide can be converted to 4-formyl perfluoro-1H, 1H-neopentyl benzene in two steps by reacting with perfluoro isobutylene gas and cesium fluoride in monoglyme followed by transmetallation with n-butyl lithium in the presence of dimethylformamide. The formyl compound can be converted to 4-[PFNP]phenyl alanine via the Erlenmeyer azlactone intermediate. The derivatized phenylalanine can be incorporated in to polyamino acids and also into peptides and proteins.

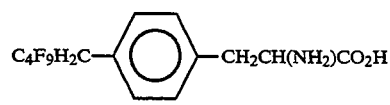

Alternatively the water soluble amino group containing macromolecules can be reacted in aqueous solution with an active ester such as a N-hydroxysuccinimide ester of an acid containing the perfluoro1H,1H-neopentyl aryl substituents to furnish stable amides as MRI agents.

EXAMPLE 4

The following example shows the incorporation of the perfluoro-1H,1H-neopentyl aryl substituents into a diethylenetriamine pentaacetic acid derivative. Diethylenetriamine pentaacetic acid anhydride can be reacted with an amino derivative of [PFNP] benzene. This type of compounds can complex with metals such as $Gd^{3+}$ which can serve as $^{19}F$ MRI and as a paramagnetic contrast agent.

O-Methyl-3,5-bis(PFNP)Benzaldoxime

To a solution of 1-formyl-3,5-bis (PFNP) benzene, (5.25 g, 0.009 mol) in anhydrous ethanol (70 mL), O-methyl hydroxylamine hydrochloride (0.85 g, 0.012 mol) was added followed by dry pyridine (70 mL). The mixture was kept under reflux for 20 hours. The solvents were removed in a rotary evaporator under reduced pressure. Residue was washed with water and filtered. Recrystallisation from ethanol furnished the title compound as colourless crystals (4.81 g, 0.008mol, 91%), m.p. 101°-103° C.

The $^1H$ NMR spectrum of its $CDCl_3$ solution showed the following resonances relative to TMS: 8.00 (S, 1H, =CH), 7.47 (S, 2H, Aromatic), 7.25 (S, 1H, Aromatic), 3.97 (S,3H, $OCH_3$), 3.40(S,4H, $2CH_2$) ppm. Its $^{19}F$ NMR spectrum in the same solvent showed a single resonance at −65.57 (s, 18F) ppm relative to freon.

1-Aminomethyl-3,5-bis (PFNP) benzene

To a suspension of sodium borohydride (1.86 g, 0.05 mol) in anhydrous tetrahydrofuran (20 mL) which was kept in a dry flask under argon, trifluoroacetic acid (5.0 g, 0.043 mol) was added dropwise. The temperature of the mixture was kept at 10° C. during the addition. Subsequently, O-Methyl-3,5-bis (PFNP) benzaldoxime (4.6 g, 0.0076 mol) in anhydrous tetrahydrofuran (50 mL) was added dropwise while stirring. After addition the mixture was refluxed for 3 hours and was finally left stirring overnight at room temperature. After excess sodiumborohydride was decomposed with dilute acetic acid, the solvents were removed under reduced pressure. The residue was extracted with dichloromethane (90 mL) and dried (anhydrous sodium sulfate). Removal of the solvent gave a gummy solid of the title compound which was recrystallized from hot hexane. (1.71 g, 0.003 mol, 39%).

The $^1H$ NMR spectrum of its $CDCl_3$ solution showed the following resonances relative to TMS: 7.28 (S, 2H, Aromatic), 7.15 (S, 1H, Aromatic), 3.87 (S, 2H, $NCH_2$), 3.41 (S, 4H, $2CH_2$). $^{19}F$ spectrum in the same solvent showed a single resonance at −65.51 (s, 18F) ppm relative to freon.

Trisodium $N^3,N^9$-bis[3',5'-bis(PFNP)benzyl aminocarbonylmethyl]-$N^6$-(carboxymethyl)-3,6,9-triazaundecanedioic acid A solution of 1-aminomethyl-3,5-bis(PFNP) benzene (1.1 g, 0.001 mol) in dimethylformamide (5 mL) was added to diethylenetriaminepentaacetic acid anhydride (0.35 g, 0.0009 mol) in dimethylformamide (5 mL) containing triethylamine (0.5 mL) with stirring. The mixture was allowed to stand overnight at room temperature. Dimethylformamide was removed under reduced pressure and the residue was dissolved in pure acetone (30 mL) and the insoluble particles was filtered off. Adding the acetone filtrate to a stirring solution of sodium chloride (1N, 150 mL) resulted in the precipitation of a gummy solid. Addition of dilute hydrochloric acid (1N, 5 mL) to the gummy product, precipitated the pure $N^3,N^9$-bis[3',5'-bis(PFNP)benzylaminocarbonylmethyl]-$N^6$-(carboxymethyl)-3,6,9-triazaundecanedioic acid as colourless crystals (1.2 g, 0.0008 mol., 87%). The crude acid was dissolved in methanol (10 mL) and titrated with sodiumhydroxide solution (1N) to pH 7.5. Methanol and water removed and the residue was dried in high vacuum to furnish the title trisodium salt (1.31 g, 0.00085 mol., 86%).

The gadolinium complex of trisodium $N^3,N^9$-bis[3',5'-bis(PFNP)benzylaminocarbonylmethyl]-$N^6$-(carboxymethyl)-3,6,9-triazaundecanedioic acid The $N^3,N^9$-bis[3',5'-bis(PFNP)benzylaminocarbonylmethyl]-$N^6$-(carboxymethyl)-3,6,9-triazaundecanedioic acid trisodium salt (1.31 g, 0.00085 mol) was dissolved in a 1:1 methanol/water mixture (25 mL) and gadolinium(III) chloride hexahydrate (0,326 g, 0.00087 mol) was added. The mixture was gently warmed to 50° C. for 1 hour and the solvent was removed, the residue was dried in vacuum to furnish the gadolinium complex with some sodium chloride. See FIG. 4.

EXAMPLE 5

One way of making $^{19}$F-labeled dendrimers is to use polyamidoamine dendrimers (PAMAM), as described in U.S. Pat. No. 4,558,120 by D. A. Tomalia (hereby incorporated by reference), and react them on their surface with a $^{19}$F-labeled acid such as 4-PFNP-phenylacetic acid: An anhydrous solution of equimolar 4-PFNP-phenyl acetic acid and N-hydroxybenzotriazole in tetrahydrofuran is treated with one equivalent of dicyclohexylcarbodiimide. After stirring for 5 h at room temperature the precipitate of dicyclohexylurea is removed by filtration. A batch of polyamidoamine dendrimers (PAMAM) containing an equimolar amount of free amino groups is added to the anhydrous mixture. After stirring for 24 h, the mixture is quenched with water and worked up by procedures well-known to one skilled in the art.

Although the invention has been described in terms of the specific embodiments many modifications and variations of the present invention are possible in light of the teachings. It is, therefore, to be understood that within the scope of the appended claims the invention may be practiced otherwise than as specifically described.

We claim:

1. A compound of the general formula:

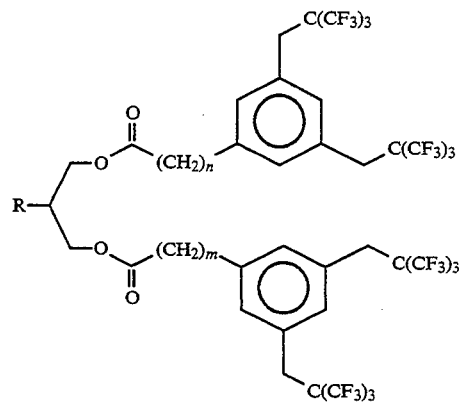

wherein R is a fatty acyl group with 3–20 carbon atoms, n is 0–18 and m is 0–18.

2. The compound of claim 1 wherein R includes a saturated fatty acid.

3. The compound of claim 1 wherein R includes an unsaturated fatty acid.

4. The compound of claim 1 wherein n=6 and m=6.

5. A compound of the general formula:

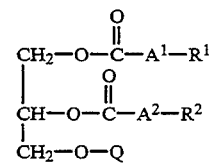

wherein Q is

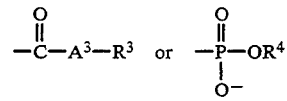

wherein $A^1$, $A^2$ and $A^3$ are each selected from the group consisting of
   saturated and unsaturated aliphatic hydrocarbon chains,
   amine substituted saturated and unsaturated aliphatic hydrocarbon chains, and
   amide substituted saturated and unsaturated aliphatic hydrocarbon chains, and
wherein $R^1$, $R^2$ and $R^3$ have the formula:

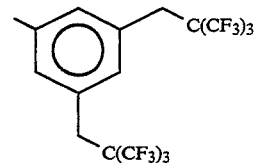

wherein $R^4$, if present, is selected from the group consisting of
   Hydrogen,
   Choline,
   Ethanolamine,
   Serine,
   Glycerol,
   or myo-Inositol.

6. A biological or pharmaceutical compound derivatized to contain at least one group having the formula:

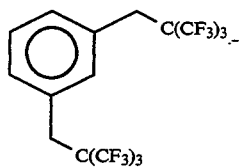

7. The compound of claim 6, wherein said compound contains iodine.

8. The compound of claim 6 wherein said compound is a dendrimer.

9. The compound of claim 6 wherein said compound is a paramagnetic chelator.

10. A composition suitable for use as an MRI contrast agent comprising the compound of claims 1-6, 8 or 9 and a suitable carrier.

11. A method of magnetic resonance imaging comprising the steps of:
(a) administering an effective amount of the composition of claim 10 to a mammal; and
(b) when said composition has reached the site to be imaged, performing magnetic resonance imaging of said site.

* * * * *